US010820932B2

(12) United States Patent
Reimels

(10) Patent No.: US 10,820,932 B2
(45) Date of Patent: *Nov. 3, 2020

(54) SURGICAL SCREW

(71) Applicant: Alphatec Spine, Inc., Carlsbad, CA (US)

(72) Inventor: William Reimels, Oceanside, CA (US)

( * ) Notice: Subject to any disclaimer, the term of this patent is extended or adjusted under 35 U.S.C. 154(b) by 116 days.

This patent is subject to a terminal disclaimer.

(21) Appl. No.: 16/241,741

(22) Filed: Jan. 7, 2019

(65) Prior Publication Data
US 2019/0133656 A1 May 9, 2019

Related U.S. Application Data

(63) Continuation of application No. 15/706,555, filed on Sep. 15, 2017, now Pat. No. 10,172,656.

(51) Int. Cl.
*A61B 17/86* (2006.01)
*A61B 17/84* (2006.01)
*A61B 17/70* (2006.01)
*A61B 17/16* (2006.01)

(52) U.S. Cl.
CPC ........ *A61B 17/844* (2013.01); *A61B 17/7062* (2013.01); *A61B 17/8605* (2013.01); *A61B 17/8625* (2013.01); *A61B 17/8685* (2013.01); *A61B 17/1671* (2013.01); *A61B 2017/8655* (2013.01)

(58) Field of Classification Search
CPC .............. A61B 17/844; A61B 17/8685; A61B 17/7258; A61B 17/7266; A61B 17/7275
USPC ................................................. 411/34, 30, 38
See application file for complete search history.

(56) References Cited

U.S. PATENT DOCUMENTS

| | | | | |
|---|---|---|---|---|
| 6,660,008 B1* | 12/2003 | Foerster | ............. | A61B 17/0401 411/34 |
| 9,439,770 B2* | 9/2016 | Biedermann | ........ | A61B 17/744 |
| 10,172,656 B1* | 1/2019 | Reimels | ............... | A61B 17/844 |
| 2008/0288003 A1* | 11/2008 | McKinley | .......... | A61B 17/8625 606/313 |
| 2010/0324607 A1* | 12/2010 | Davis | ................. | A61B 17/8625 606/313 |
| 2011/0319946 A1* | 12/2011 | Levy | .................. | A61B 17/7049 606/309 |
| 2012/0101530 A1* | 4/2012 | Robling | ............... | A61B 17/844 606/279 |

(Continued)

FOREIGN PATENT DOCUMENTS

EP 2910209 A1 * 8/2015 ......... A61B 17/7258

*Primary Examiner* — Jan Christopher L Merene
(74) *Attorney, Agent, or Firm* — John Chau

(57) ABSTRACT

A surgical screw configured to expand and prevent or minimize bone growth inside of the surgical screw is provided. Accordingly, the surgical screw is configured to increase the purchase of the surgical screw with respect to the bone, but also to be withdrawn from the bone without damaging the bone as a result of bone ingrowth. The surgical screw includes a center post with an inner bore and an outer sleeve concentric to the center post. An outer surface of the outer sleeve includes a thread to engage bone. The outer sleeve includes a cut pattern defining an expandable region configurable between a first state with a first radius measured from a longitudinal axis of the surgical screw to the outer surface and a second state having a second radius measured from the longitudinal axis to the outer surface.

20 Claims, 5 Drawing Sheets

(56) References Cited

U.S. PATENT DOCUMENTS

2014/0012336 A1* 1/2014 Biedermann ...... A61B 17/8685
606/313

* cited by examiner

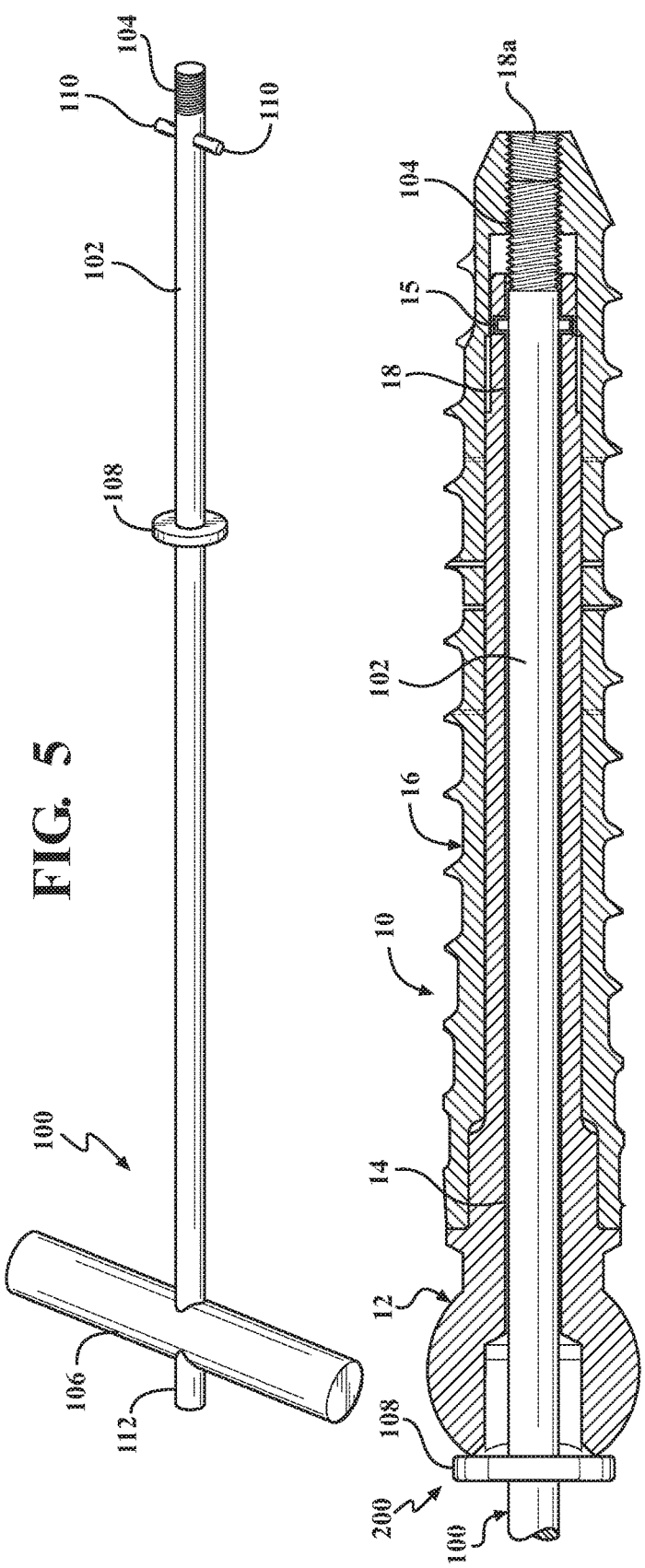

SURGICAL SCREW

CROSS-REFERENCE TO RELATED APPLICATIONS

This application is a continuation of U.S. application Ser. No. 15/706,555, filed Sep. 15, 2017, the contents of which are incorporated herein by reference.

TECHNICAL FIELD

The present disclosure generally relates to a surgical screw configured to radially expand for use in a spinal procedure.

BACKGROUND

The spine is a flexible column formed of a plurality of bones called vertebrae. The vertebrae are hollow and stack one upon the other, forming a strong hollow column for support of the cranium and trunk. The hollow core of the spine houses and protects the nerves of the spinal cord. The different vertebrae are connected to one another by means of articular processes, ligaments, and intervertebral, fibrocartilaginous bodies known as disks. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae. The spine is held upright through the work of the back muscles, which are attached to the vertebrae.

The spinal disks act as shock absorbers, cushioning the spine, and preventing individual bones from contacting each other. Disks also help to hold the vertebrae together. The weight of the upper body is transferred through the spine to the hips and the legs. Disks may degenerate, herniate, bulge, or burst and impinge on the nerves between the vertebrae causing pain.

While the normal spine has no side-to-side curve, it does have a series of front-to back curves, giving it a gentle "S" shape. If the proper shaping and/or curvature are not present due to scoliosis, neuromuscular disease, cerebral palsy, or other disorder, it may be necessary to straighten or adjust the spine into a proper curvature. Generally the correct curvature is obtained by manipulating the vertebrae into their proper position and securing that position with a rigid system of screws, rods, intervertebral spaces, and/or plates. The various components of the system may be surgically inserted through open or minimally invasive surgeries. The components may also be inserted through various approaches to the spine including anterior, lateral, and posterior approaches and others in between.

Some screws may be expandable in order to enhance stability within the vertebra, for example when the vertebra suffers from degeneration, osteoporosis, and other conditions that cause the bone to become brittle. These expandable bone screws may allow bone ingrowth through expanded cells of the screw. In some instances such as revision surgeries, it may be necessary to remove the expanded screw. However, once the bone becomes mineralized, it reduces the ability of the expanded cells to collapse back to the base diameter of the screw.

SUMMARY

Provided herein are expandable surgical screws and methods for preventing bone ingrowth inside the surgical screw. A surgical screw includes generally a center post. The center post is a generally elongated inner member with an inner bore. The surgical screw further includes an outer sleeve concentric to the center post. The outer sleeve includes a cut pattern. A head is disposed on a proximal end of the center post. The head includes a through-hole open to the bore of the center post.

The center post extends along a longitudinal axis of the outer sleeve. An outer surface of the outer sleeve includes a thread to engage bone. The cut pattern defines an expandable region configurable between a first state with a first radius measured from the longitudinal axis to the outer surface and a second state having a second radius that is larger than the first radius measured from the longitudinal axis to the outer surface.

The head is coupled to the center post at a neck. The through-hole of the head is configured to receive a driving instrument to insert and drive the surgical screw into the bone. The instrument is further configured to drive the center post and outer sleeve towards the distal end of the surgical screw so as to actuate the cut pattern, wherein the expandable region moves from the first state to the second state.

In one embodiment, the cut pattern defines a plurality of generally spear shaped portions in the outer sleeve. The spear shaped portions are formed into a first group and a second group, wherein each of the pointed ends of the first and second group face each other and are axially offset from each other.

In one embodiment, the distal end of the surgical screw may include cut-outs. The cuts-outs define a first planar surface and a second planar surface. The first and second planar surfaces are generally orthogonal to each other.

In other features, the cut patterns include a first elongated slit opposite a second elongated slit so as to define a first and a second side of the spear shaped portion. The ends of the first and second elongated slits come together so as to form a pointed end. The spear shape portion includes a rounded end spaced apart from the pointed end so as to form a pocket.

BRIEF DESCRIPTION OF THE DRAWINGS

FIG. 5 is a perspective view of an embodiment of a deployment instrument.

FIG. 6A is a cross-sectional view of the surgical screw shown in FIG. 2A with a deployment instrument engaged in the inner bore of the center post.

FIG. 6B is a cross-sectional view of the surgical screw shown in FIG. 6B showing the instrument actuating the surgical screw into the second state.

DETAILED DESCRIPTION

Figure 1:
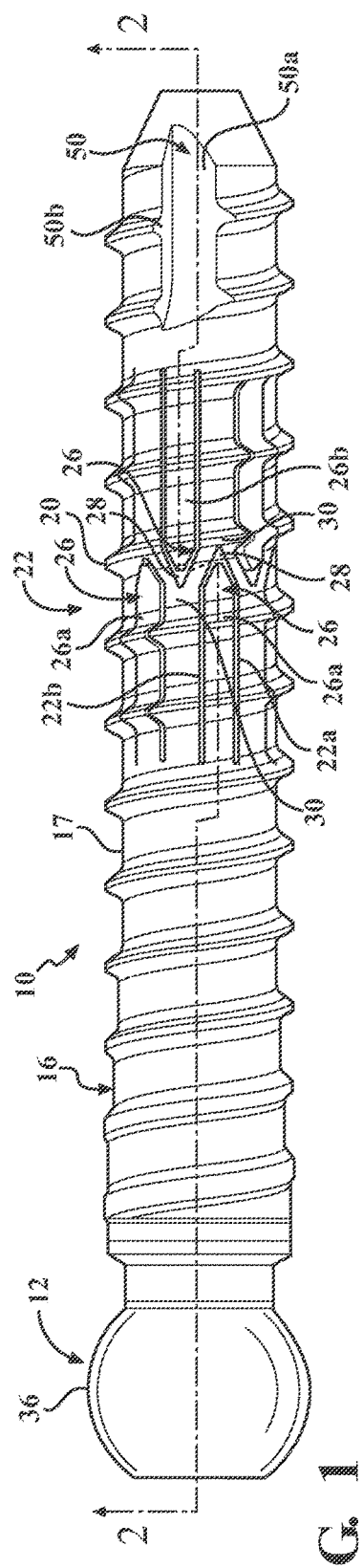
FIG. 1 is a side view of one embodiment of the surgical screw.

With reference to FIG. 1, a surgical screw 10 is provided. The surgical screw 10 is configured to expand and prevent or minimize bone growth inside of the surgical screw 10. Accordingly, the surgical screw 10 is configured to expand radially into bone so as to increase the purchase of the surgical screw 10 with respect to the bone, but also contract or retract so as to be withdrawn from the bone without damaging the bone as a result of bone ingrowth.

With reference now to FIGS. 1A-3, a surgical screw 10 according to one embodiment is provided. The surgical screw 10 is a generally elongated member having a distal end opposite a proximal end. The words proximal and distal are used herein to denote specific ends of components of the surgical screw 10. A distal end refers to the end of the surgical screw 10 adapted to be inserted into the body of the patient. A proximal end refers to the end of the surgical screw 10 opposite of the distal end.

The surgical screw 10 includes a center post 12 with an inner bore 14 and an outer sleeve 16 concentric to the center post 12. The center post 12 is a continuous surface bounding the inner bore 14 and is open at the distal end.

The outer sleeve 16 is open at the proximal end of the surgical screw 10 and includes a second bore 18 for receiving the center post 12. The second bore 18 is dimensioned to sliding fit the center post 12. In embodiments, the center post 12 is fixedly attached to the outer sleeve 16, e.g., via welding, adhesives or the like, such that the center post 12 and outer sleeve 16 rotate as a single unit. In other embodiments, the second bore 18 is dimensioned to have an interference fit with the center post 12 such that the center post 12 and outer sleeve 16 rotate as single unit. An outer surface 17 of the outer sleeve 16 includes a thread 20 to engage bone. The pitch and the angle of the thread 20 shown herein are illustrative and not limiting to the scope of the appended claims. It should be appreciated that although a single thread 20 is shown, the surgical screw 10 may be double threaded.

The outer sleeve 16 includes a cut pattern 22. The cut pattern 22 is illustratively shown formed along a midportion of the outer sleeve 16. The cut pattern 22 defines an expandable region 24 configurable between a first state (FIG. 2A) with a first radius r1 measured from a longitudinal axis 1 to an outer surface 17 of the outer sleeve 16 and a second state (FIG. 2B) having a second radius r2 larger than the first radius r1 measured from the longitudinal axis 1 to the outer surface 17 of the outer sleeve 16. The cut pattern 22 is configured to actuate the outer sleeve 16 so as to move the outer sleeve 16 between the first state and the second state.

Figure 3:
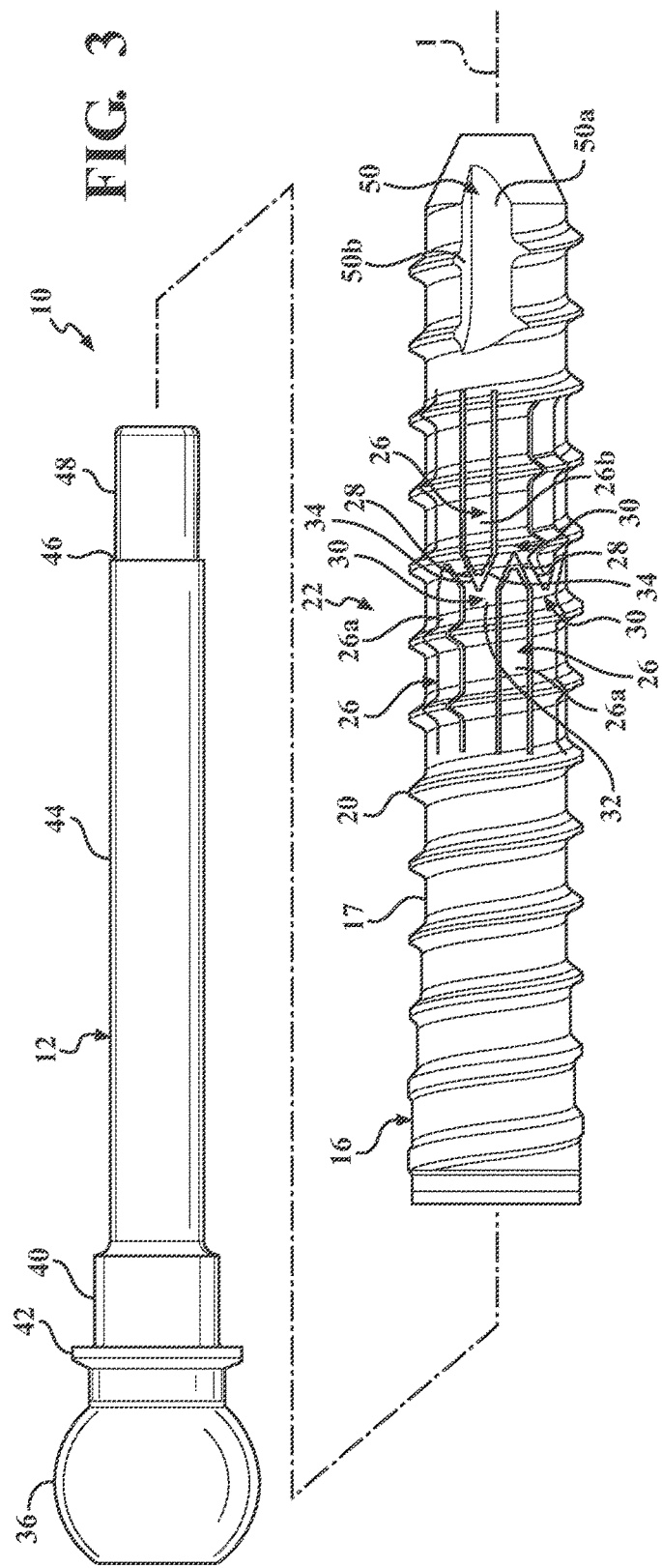
FIG. 3 is an exploded view of the surgical screw shown in FIG. 1.

The cut pattern 22 traverses the outer surface 17 of the outer sleeve 16, as shown in FIGS. 1 and 3. In one embodiment, the cut pattern 22 defines a plurality of generally spear-shaped portions 26 of the outer sleeve 16. The cut patterns 22 include a first elongated slit 22a opposite a second elongated slit 22b so as to define a first and a second side of the spear-shape portion 26. The ends of the first and second elongated slits 22a, 22b come together so as to form a pointed end.

The spear-shaped portions 26 are a generally elongated member having a pointed end. The spear-shaped portions 26 are formed into a first group 26a and a second group 26b, wherein each of the pointed ends of the first and second groups 26a, 26b face each other and axially offset from each other. The spear-shaped portions 26 have a thickness commensurate with the thickness of the outer sleeve 16. In one embodiment, the spear-shaped portion 26 includes a rounded end spaced apart from the pointed end formed by the first and second elongated slits 22a, 22b so as to form a pocket 28. FIG. 1A also shows that the thread 20 is continuous and extends onto the spear-shaped portions 26.

Figure 7:
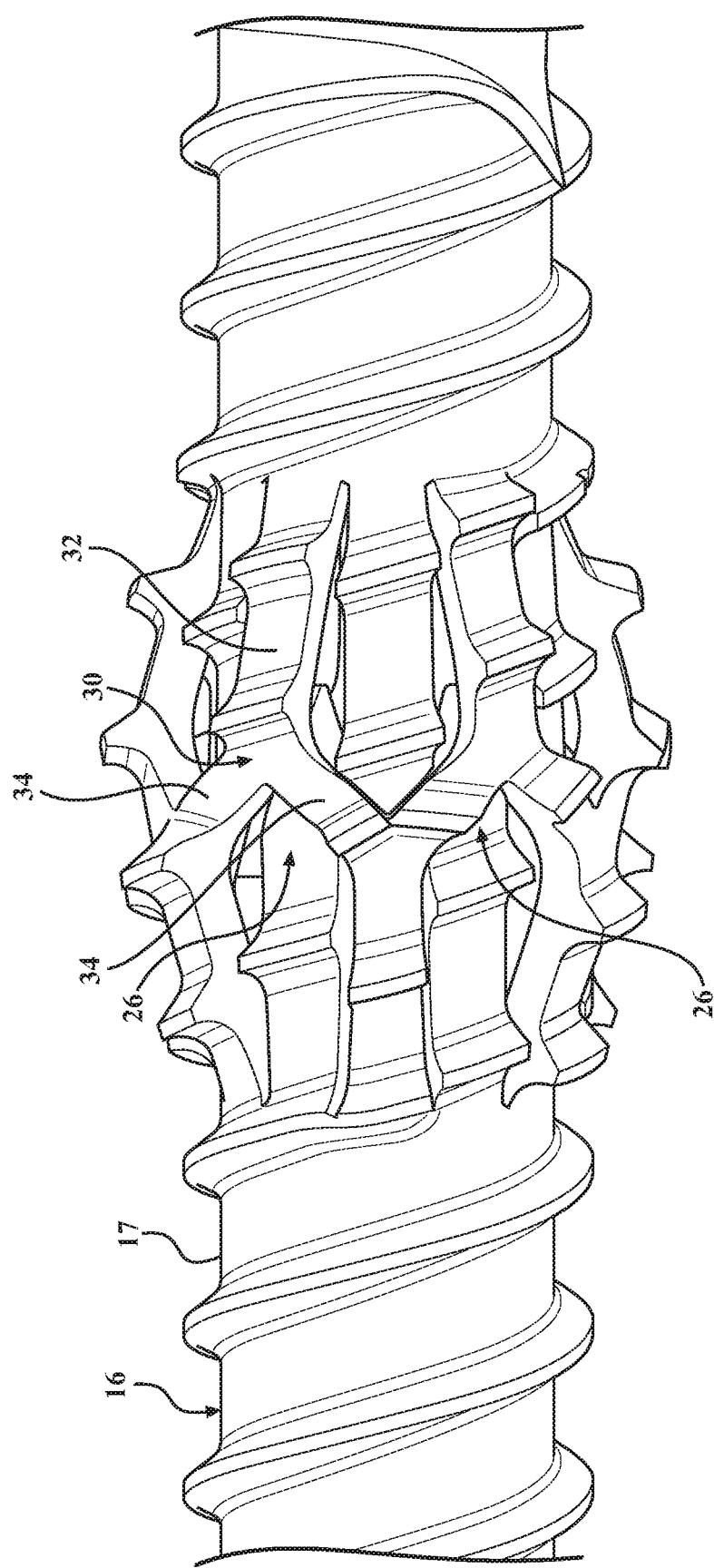
FIG. 7 is a perspective view of the surgical screw in a second state.

The cut pattern 22 further defines a plurality of Y-shaped members 30 which are interconnected to each other. The Y-shaped members 30 include a stem 32 and a pair of arms 34. The arms 34 extend at an angle from an end of the stem 32 forming the general shape of a "V". FIGS. 1 and 3 show the Y-shaped members 30 in the first state. FIG. 7 shows the Y-shaped members 30 in the second state. FIGS. 1, 3 and 7 further illustrate how each end of the arms 34 of the Y-shaped members 30 are contiguous with each other.

Figure 4:
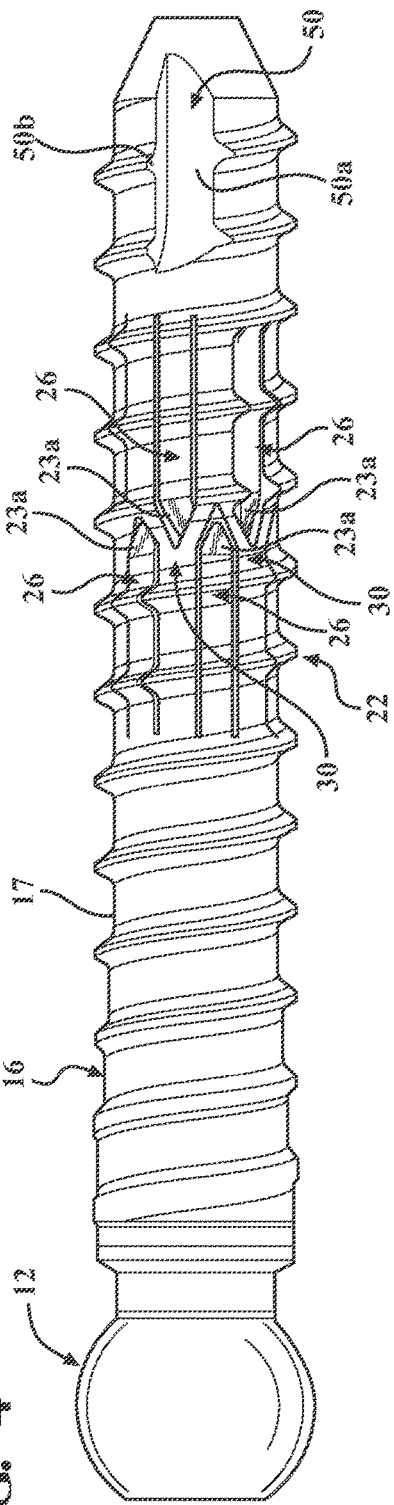
FIG. 4 is a perspective view of a second embodiment of a cut pattern of a surgical screw.

With reference now to FIG. 4, an embodiment of the cut pattern 22 includes an angled surface 23a. The angled surface 23a is formed on the tip of the end of the spear shaped portions 26. The angled surface 23a is configured to slide underneath an opposing Y-shaped member 30 when the outer sleeve 16 is compressed. As such, the Y-shaped members 30 are lifted or forced outwardly by the spear-shaped portions 26.

In one example, the cut pattern 22 is formed by a laser. Lasers that may be used to dispose the cut patterns 22 include pulse lasers such as femto-second lasers and continuous wave lasers. In other examples, the cut pattern 22 is mechanically cut with a cutting tool.

A head 36 is disposed on a proximal end of the center post 12 and includes a through hole 38 open to the inner bore 14 of the center post 12. The proximal end of the through-hole 38 of the head 36 may be dimensioned so as to receive the working end of an instrument adapted to engage the head 36 so as to push the center post 12 distally into the second bore 18 of the outer sleeve 16. In one embodiment, the proximal end of the through-hole 38 is adapted to seatingly engage a nut or an allen wrench which may be used to turn and implant the surgical screw 10 within bone material.

The head 36 is coupled to the center post 12 at a neck 40. The through-hole 38 of the head 36 is configured to receive a deployment instrument 100 (shown in FIGS. 5-6B) to insert and drive the center post 12 into the bone. The deployment instrument 100 is further configured to drive the center post 12 towards the distal end of the outer sleeve 16 so as to compress the outer sleeve 16 and actuate the cut pattern 22, wherein the expandable region 24 moves from the first state to the second state.

FIG. 3 is an exploded view of the screw. The center post 12 is configured to slide into the second bore 18 of the outer sleeve 16. The neck 40 of the center post 12 includes a lip 42 separating the neck 40 from the head 36. The lip 42 extends radially from the outer surface of the neck 40.

The center post 12 further includes an elongated tubular portion 44 having a diameter which is smaller than that of the neck 40. A radial edge 45 defines an end portion 48 of the center post 12. The end portion 48 of the center post 12 is smaller in diameter than the elongated tubular portion 44 of the center post 12. The inner bore 14 extends through the center post 12 so as to define an open proximal and distal end of the center post 12.

Figure 2A:
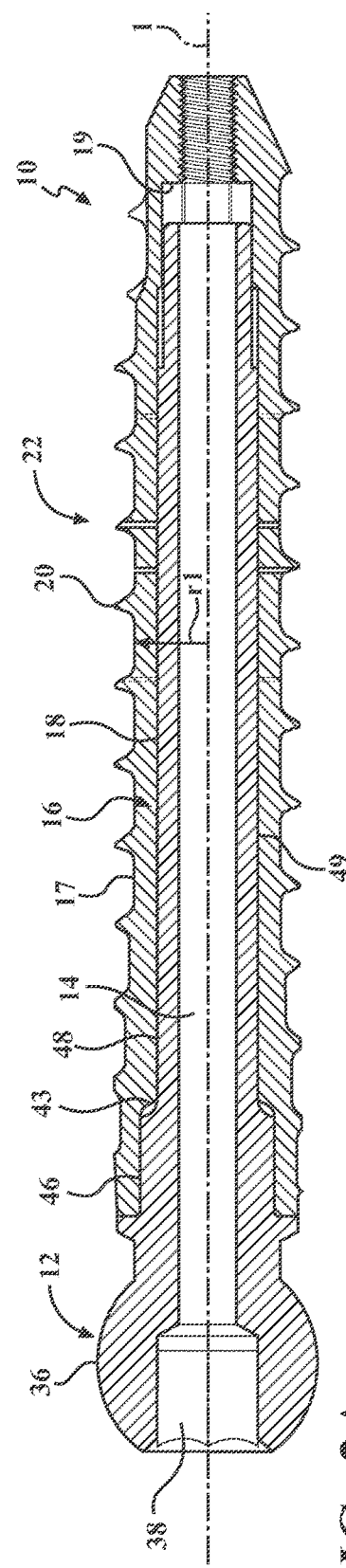
FIG. 2A is a cross-sectional view of the surgical screw shown in FIG. 1 taken along line 2-2 in a first state.
Figure 2B:
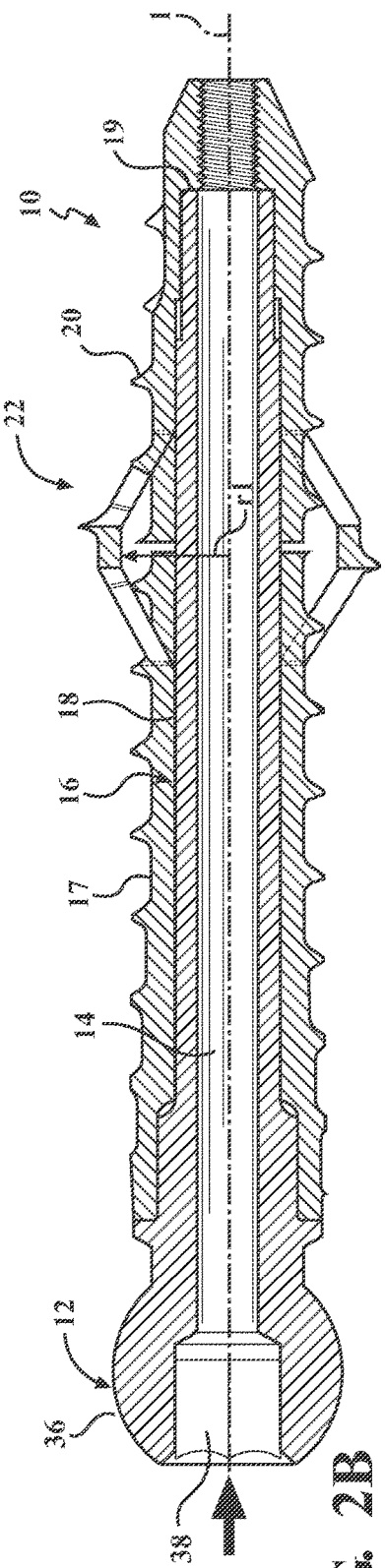
FIG. 2B is a cross-sectional view of the surgical screw shown in FIG. 2A in a second state.

With reference again to FIG. 3 and also to FIGS. 2A and 2B, the center post 12 is adapted to slidingly fit within the second bore 18 of the outer sleeve 16. As shown, the axial length of the center post 12, as measured from the lip 42 of the neck 40 to the distal end of the center post 12, is shorter than the second bore 18. FIG. 2A shows the distal end of the center post 12 being spaced apart from an inner end wall 19 of the outer sleeve 16.

FIG. 2A is a cross-section of the surgical screw 10 shown in FIG. 1 taken along line 2-2. FIG. 2A shows the inner dimensions of the second bore 18 when the surgical screw 10 is in the first state. In particular, the second bore 18 of the outer sleeve 16 is configured to engage the center post 12 and control or limit the advancement of the center post 12 within the second bore 18. In embodiments, the lip 42 engages a proximal end of the outer sleeve 16 to limit the advancement of the center post 12 within the second bore 18. In one embodiment, the proximal end of the outer sleeve 16 includes an inner lip 43 so as to define a head portion 46 and a body portion 49 of the second bore 18. The head portion 46 of the second bore 18 is larger in diameter than the body portion of the second bore 18.

FIG. 2B is a view of the surgical screw 10 shown in FIG. 2A in the second state. The arrow displayed adjacent the proximal end of the screw indicates a load applied to the head 36 of the center post 12. The load advances the distal end of the center post 12 into the second bore 18 pressing the distal end of the center post 12 into engagement with the inner end wall 19 disposed within the second bore 18 of the outer sleeve 16. The advancement of the center post 12 actuates (compresses) the outer sleeve 16 wherein the cut pattern 22 expands the surgical screw 10 into the second state.

In one embodiment, the distal end of the outer sleeve 16 may include cut-outs 50. The cuts-outs 50 define a first planar surface 50a and a second planar surface 50b. The first and second planar surfaces 50a, 50b are generally orthogonal to each other. The cut-outs 50 facilitate the entry of the surgical screw 10 into bone.

With reference now to FIGS. 5-6B an operation of the surgical screw 10 is provided. The surgical screw 10 is shown being actuated by a deployment instrument 100 so as to define a system 200 for performing a spinal procedure. The system 200 is configured to actuate the surgical screw 10 between the first state (FIG. 6A) and the second state (FIG. 6B). The deployment instrument 100 is configured to compress the outer sleeve 16 so as to actuate the cut pattern 22 between the first state and the second state.

In one instance, the deployment instrument 100 may be used to compress the outer sleeve 16 so as to actuate the surgical screw 10 from the first state to the second state, such as after the surgical screw 10 has been screwed into bone. The radial expansion of the surgical screw 10 helps the surgical screw 10 find purchase in the bone material.

In the event the surgeon desires to remove the surgical screw 10, the deployment instrument 100 may be used to contract or retract the outer sleeve 16 from the compressed state, wherein the surgical screw 10 is moved from the second state to the first state. The screw may then be simply turned and removed from the implant site. For example, in embodiments where the lip 42 of the center post 12 is fixedly attached to the outer sleeve 16, the deployment instrument 100 may have one or more retraction pins 110 that may be deployed and extend outwardly from the rod 102 via an actuator 112. Also, the center post may have a retraction groove 15 that is complimentary with the one or more retraction pins 110. Upon insertion of the deployment instrument 100 into the surgical screw 10 as depicted in FIG. 6B, the retraction pins 110 are deployed (e.g., via an actuator 112) into the retraction groove 15 such that unscrewing the deployment instrument 100 from the distal end of the outer sleeve 16 moves the retraction pins 110 and the lip 42 fixedly attached to the outer sleeve 16 in the proximal direction. Movement of the lip 42 fixedly attached to the outer sleeve 16 stretches or de-compresses the expandable region 24 of the outer sleeve 16 back to the first state.

FIG. 6A shows the deployment instrument 100 inserted into the inner bore 14 of the center post 12. In one embodiment of a deployment instrument 100, the deployment instrument 100 includes a rod 102 with a threaded end 104 and a handle 106. A collar 108 is disposed a predetermined distance from the threaded end 104. The collar 108 is fixedly mounted to the rod 102. FIG. 6A shows the threaded end 104 of the rod 102 adjacent a threaded end 18a of the second bore 18 of the outer sleeve 16.

FIG. 6B shows the advancement of the deployment instrument 100 into the threaded end 104 of the second bore 18. The rod 102 may be threaded into the second bore 18 by simply turning the handle 106. As the rod 102 is threaded deeper into the second bore 18, the collar 108 applies a load to the head 36 of the center post 12 pushing the center post 12 further into the second bore 18 of the outer sleeve 16. As the center post 12 is pushed further into the outer sleeve 16, the cut pattern 22 is actuated from the first state to the second state, radially expanding the diameter of the surgical screw 10 about the expansion regions.

FIG. 7 shows how the pointed ends of the spear-shaped portions 26 close the pocket 28 and abut against the Y-shaped members 30, which compresses the arms 34 causing the arms 34 to protrude radially from the outer sleeve 16. Though FIG. 7 shows the arms 34 of the Y-shaped members 30 creating a gap with respect to a respective spear, it should be appreciated that the spear-shaped portions and Y-shaped members 30 may be dimensioned so as to abut against each other and expand radially without creating any gaps.

Figure 8:
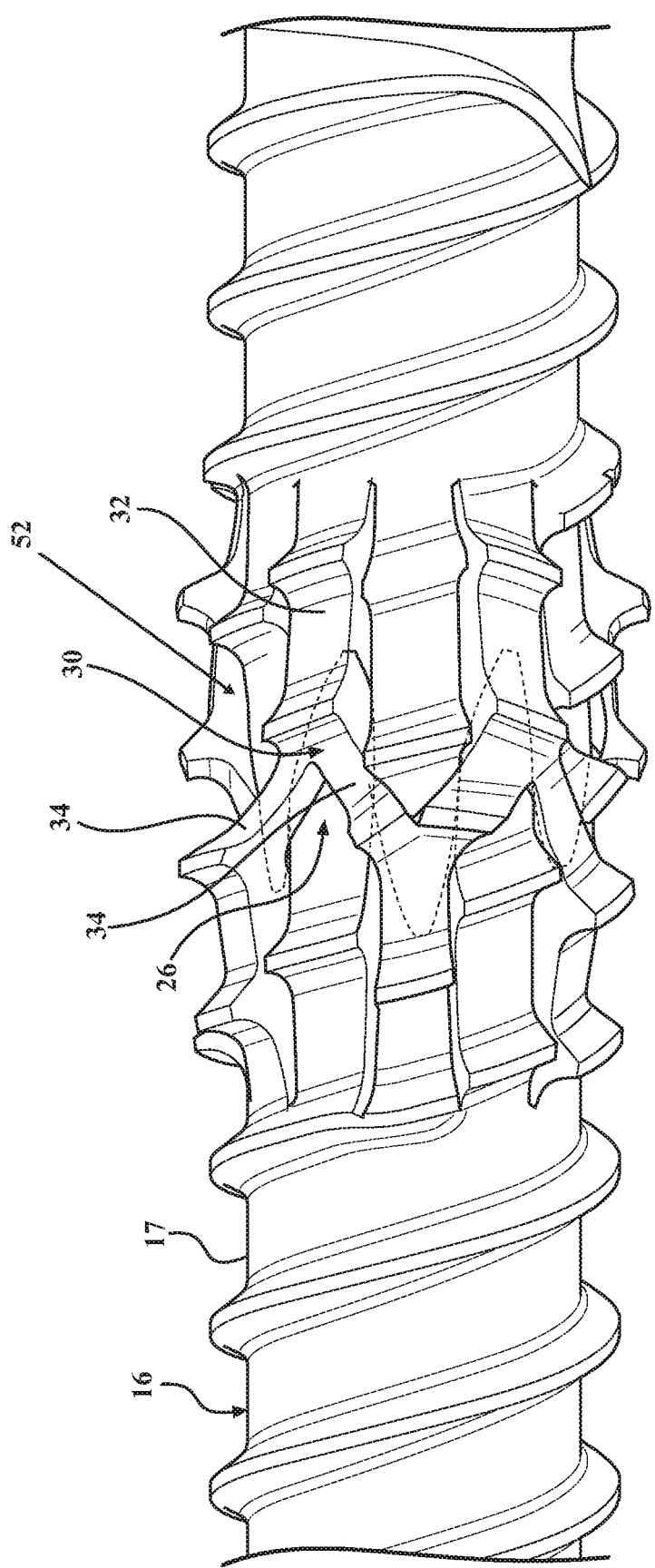
FIG. 8 is a perspective view of an embodiment of the surgical screw configured to prevent bone ingrowth.

With reference now to FIG. 8, an embodiment of a surgical screw 10 configured to inhibit bone ingrowth is provided. As used herein, the term "bone ingrowth" refers to a condition wherein bone growth intrudes into the gaps shown in FIG. 7. The surgical screw 10 includes a center post 12 with an inner bore 14 and an outer sleeve 16 concentric to the center post 12. The center post 12 is a continuous surface bounding the inner bore 14 and is open at the distal end. For illustrative purposes, the center post is not shown.

The outer sleeve 16 includes a cut pattern 22. The cut pattern 22 traverses the outer surface 17 of the outer sleeve 16. The cut pattern 22 defines a plurality of generally spear-shaped portions 26 of the outer sleeve 16. The cut patterns 22 include a first elongated slit 22a opposite a second elongated slit 22b so as to define a first and a second side of the spear-shaped portion 26. The ends of the first and second elongated slits 22a, 22b come together so as to form the pointed end of the spear-shaped portions 26. The cut pattern 22 further defines a plurality of Y-shaped members 30 which are interconnected to each other. The Y-shaped members 30 include a stem 32 and a pair of arms 34. The arms 34 extend at an angle from an end of the stem 32 forming the general shape of a "V".

The cut pattern 22 includes an angled surface 23a formed on the tip of the end of the spear-shaped portions 26. The angled surface 23a is configured to slide underneath an opposing Y-shaped member 30 when the outer sleeve 16 is compressed. FIG. 8 shows how the sides of the end of the spear-shaped portions 26 (shown in a broken line) are pressed against each other when the surgical screw 10 is compressed. Further the ends of the spear-shaped portions 26 slide underneath and are in contact with a respective arm 34 of the Y-shaped members 30. The spear-shaped portions 26 urge the Y-shaped members 30 radially outward so as to place the surgical screw in the second state as shown in FIG. 8. The side walls of the spear-spear shaped portions 26 are in contact with corresponding and adjacent stems 32 of the Y-shaped member 30 so as to form a seal 52 which prevents bone ingrowth from occurring. Thus, removal of the surgical screw 10 minimizes damage to the implant site relative to expandable screws with gaps.

It should be appreciated that the surgical screw 10 may be made from a single or multiple stainless steel alloy, nickel titanium alloy (e.g., Nitinol), surgical grade titanium alloy (for example, Ti-6Al-4V, ASTM F 136), commercially pure titanium (for example, Ti-CP2, ASTM F 67) with or without an electrolytic conversion coating, cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungstenrhenium alloys, for example, as disclosed in International Pub. No. WO 03/082363, polymers such as polyethylene teraphathalate (PET), polyester (e.g., DACRON® from E. I. DuPont de Nemours and Company, Wilmington, Del.), polypropylene, aromatic polyesters, such as liquid crystal polymers (e.g., Vectran, from Kuraray Co., Ltd., Tokyo, Japan), ultra-high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N. V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEB AX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA)s polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum, and gold.

The surgical screw 10 can be filled, coated, layered, and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rh-BMPs), other materials described herein, or combinations thereof.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:

1. A surgical screw comprising:
an outer sleeve, the outer sleeve having a thread and a cut pattern, the cut pattern defining a plurality of first and second spear-shaped portions, the plurality of first spear shaped portions extending along an axis of the outer sleeve, each of the plurality of first spear-shaped portions being formed by a pair of spaced apart first slits so as to define an elongated first body pointing proximally to a first pointed end and the plurality of second spear-shaped portions extending along an axis of the outer sleeve, each of the plurality of second spear-shaped portions being formed by a pair of spaced apart second slits so as to define an elongated second body pointing distally to a second pointed end, wherein each of the first and second pointed ends are axially and radially offset from each other and are disposed along a common radius, the plurality of first and second spear-shaped portions defining an expandable region, the expandable region configurable between a first state with a first radius measured from a longitudinal axis of the outer sleeve to an outer surface of the outer sleeve and a second state having a second radius measured from the longitudinal axis to the outer surface of the outer sleeve, the first radius being less than the second radius.

2. The surgical screw of claim 1, wherein each elongated first body is axially and radially offset from each elongated second body.

3. The surgical screw of claim 1, wherein each of the first and second pointed ends are located next to each other on the outer sleeve when the surgical screw is in the first state.

4. The surgical screw of claim 1, wherein the first pointed ends are located proximal to the second pointed ends when the surgical screw is in the second state.

5. The surgical screw of claim 1, wherein each of the plurality of first and second spear-shaped portions includes a rounded end spaced apart from a respective first and second pointed ends of the cut pattern so as to form a pocket.

6. The surgical screw of claim 5, wherein the cut pattern further defines a plurality of Y-shaped members which are interconnected to each other.

7. The surgical screw of claim 6, wherein the plurality of Y-shaped members include a stem and a pair of arms, the arms extending at an angle from an end of the stem forming the general shape of a "V".

8. The surgical screw of claim 1, further comprising a center post having an inner bore, the outer sleeve being concentric to the center post, wherein the center post further includes a head and a neck, the head including a through-hole open to the inner bore of the center post.

9. The surgical screw of claim 8, wherein the neck of the center post includes a lip separating the neck from the head, the lip extending radially from an outer surface of the neck.

10. A system for performing a spinal procedure, the system comprising:
   the surgical screw of claim 1; and
   a deployment instrument, the deployment instrument configured to compress or retract the outer sleeve so as to actuate the cut pattern between the first state and the second state.

11. The system as set forth in claim 10, wherein the deployment instrument includes a rod with a threaded end, a handle and a collar disposed a predetermined distance from the threaded end.

12. The system of claim 11, wherein the outer sleeve comprises a second bore with a threaded end configured to receive the threaded end of the rod.

13. The system of claim 12, wherein each of the plurality of first and second spear-shaped portions includes a rounded end spaced apart from a respective first and second pointed ends of the cut pattern so as to form a pocket.

14. The system of claim 13, wherein the cut pattern further defines a plurality of Y-shaped members which are interconnected to each other.

15. The system of claim 14, wherein the plurality of Y-shaped members include a stem and a pair of arms, the arms extend at an angle from an end of the stem forming the general shape of a "V".

16. The system of claim 14, wherein the surgical screw further comprises a center post with an inner bore, the outer sleeve concentric to the center poster, and wherein the center post includes a head and a neck, and the head includes a through-hole open to the inner bore of the center post.

17. A surgical screw comprising:
   a center post having an inner bore;
   an outer sleeve concentric to the center post, the outer sleeve having a thread and a cut pattern, the cut pattern defining an expandable region, the cut pattern including a slit defining a plurality of spear shaped portions nested between a plurality of Y-shaped members, the plurality of Y-shaped members being interconnected to each other, the expandable region configurable between a first state with a first radius measured from a longitudinal axis of the outer sleeve to an outer surface of the outer sleeve and a second state having a second radius measured from the longitudinal axis to the outer surface of the outer sleeve, wherein compression of the outer sleeve relative to the center post actuates the cut pattern so as to move the surgical screw between the first state and the second state, wherein an edge of one of the plurality of spears at least partially abuts an edge of an opposite one of the plurality of spears.

18. The surgical screw of claim 17, wherein fully compressing the outer sleeve relative to the center post causes the edges of the plurality of spears to be seated beneath a portion of a corresponding one of the Y-shaped members so as to form a seal to reduce bone ingrowth.

19. The surgical screw of claim 17, wherein each of the plurality of spear-shaped portions includes a rounded end spaced apart from a pointed end of the cut pattern so as to form a pocket.

20. The surgical screw of claim 17, wherein the plurality of Y-shaped members include a stem and a pair of arms, the arms extending at an angle from an end of the stem forming the general shape of a "V".

* * * * *